US010631912B2

(12) United States Patent
McFarlin et al.

(10) Patent No.: US 10,631,912 B2
(45) Date of Patent: Apr. 28, 2020

(54) INTERFACE MODULE FOR USE WITH NERVE MONITORING AND ELECTROSURGERY

(75) Inventors: Kevin Lee McFarlin, Jacksonville, FL (US); John C. Bruce, Louisville, CO (US); David C. Hacker, Jacksonville, FL (US); Robert Allen Tucker, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 1771 days.

(21) Appl. No.: 12/771,713

(22) Filed: Apr. 30, 2010

(65) Prior Publication Data
US 2011/0270120 A1  Nov. 3, 2011

(51) Int. Cl.
*A61B 18/12* (2006.01)
*A61B 5/0488* (2006.01)
*A61B 5/00* (2006.01)
*A61N 1/36* (2006.01)
*A61B 18/00* (2006.01)
(Continued)

(52) U.S. Cl.
CPC ........ *A61B 18/1206* (2013.01); *A61B 5/0488* (2013.01); *A61B 5/40* (2013.01); *A61B 5/4893* (2013.01); *A61N 1/36* (2013.01); *A61B 18/1445* (2013.01); *A61B 34/30* (2016.02); *A61B 2018/00589* (2013.01);
(Continued)

(58) Field of Classification Search
CPC ............ A61B 18/1206; A61B 18/1233; A61B 2018/00434; A61B 2018/0044; A61B 2018/00446; A61B 2018/00589; A61B 2018/00601; A61B 2018/00839; A61B 2018/1273; A61B 5/0488; A61B 5/40; A61B 5/4893; A61N 1/36; A61N 1/36003

USPC .................................................... 606/32–40
See application file for complete search history.

(56) References Cited

U.S. PATENT DOCUMENTS

| 4,383,534 A | 5/1983 | Peters |
| 5,024,228 A | 6/1991 | Goldstone et al. |

(Continued)

FOREIGN PATENT DOCUMENTS

| DE | 102008018262 | 10/2009 |
| EP | 2 366 329 | 12/2014 |

(Continued)

OTHER PUBLICATIONS

Akagami, Ryojo, Charles C.J. Dong, and Brian D. Westerberg "Localized Transcranial Electrical Motor Evoked Potentials for Monitoring Cranial Nerves in Cranial Base Surgery" Operative Neurosurgery 1, vol. 57, Jul. 2005 (pp. 78-85).

(Continued)

*Primary Examiner* — Michael F Peffley
*Assistant Examiner* — Samantha M Good
(74) *Attorney, Agent, or Firm* — Dicke, Billig & Czaja, PLLC

(57) ABSTRACT

Concepts presented herein relate to an interface module that can be electrically coupled to an electrical stimulation generator, a radio frequency generator and an instrument. A selection module is coupled to the interface module and operates in a first mode to deliver electrical stimulation signals from the electrical stimulation generator to the instrument and in a second mode to deliver radio frequency signals from the radio frequency generator to the instrument.

19 Claims, 2 Drawing Sheets

(51) Int. Cl.
*A61B 18/14* (2006.01)
*A61B 34/30* (2016.01)

(52) U.S. Cl.
CPC .......... *A61B 2018/00601* (2013.01); *A61B 2018/00839* (2013.01); *A61B 2018/1273* (2013.01)

(56) References Cited

U.S. PATENT DOCUMENTS

| | | | |
|---|---|---|---|
| 5,284,154 | A | 2/1994 | Raymond et al. |
| 5,560,372 | A | 10/1996 | Cory |
| 5,775,331 | A | 7/1998 | Raymond et al. |
| 5,836,943 | A | 11/1998 | Miller et al. |
| 5,925,045 | A | 7/1999 | Reimels et al. |
| 5,991,650 | A | 11/1999 | Swanson et al. |
| 6,038,477 | A | 3/2000 | Kayyali |
| 6,139,545 | A | 10/2000 | Utley et al. |
| 6,292,701 | B1 | 9/2001 | Prass et al. |
| 6,306,100 | B1 | 10/2001 | Prass |
| 6,334,068 | B1 | 12/2001 | Hacker |
| 6,609,018 | B2 | 8/2003 | Cory et al. |
| 6,810,281 | B2 | 10/2004 | Brock et al. |
| 7,206,641 | B2 | 4/2007 | Ignagni et al. |
| 7,214,197 | B2 | 5/2007 | Prass |
| 7,216,001 | B2 | 5/2007 | Hacker et al. |
| 7,226,447 | B2 | 6/2007 | Uchida et al. |
| 7,310,546 | B2 | 12/2007 | Prass |
| 7,470,236 | B1 | 12/2008 | Kelleher et al. |
| 7,522,953 | B2 | 4/2009 | Kaula et al. |
| 8,090,436 | B2 | 1/2012 | Hoey et al. |
| 8,374,673 | B2 | 2/2013 | Adcox et al. |
| 8,603,083 | B2 | 12/2013 | Park et al. |
| 8,712,496 | B2 | 4/2014 | Langer |
| 8,755,904 | B2 | 6/2014 | Baag |
| 8,886,280 | B2 | 11/2014 | Kartush |
| 2002/0095199 | A1 | 7/2002 | West, Jr. et al. |
| 2005/0283148 | A1 | 12/2005 | Janssen et al. |
| 2006/0015162 | A1 | 1/2006 | Edward et al. |
| 2006/0184164 | A1 | 8/2006 | Malis et al. |
| 2007/0021803 | A1 | 1/2007 | Deem et al. |
| 2007/0100334 | A1* | 5/2007 | McFarlin et al. .......... 606/45 |
| 2007/0208333 | A1* | 9/2007 | Uchida et al. .......... 606/34 |
| 2007/0239187 | A1 | 10/2007 | Brunnett et al. |
| 2008/0009853 | A1 | 1/2008 | Martin et al. |
| 2008/0300655 | A1 | 12/2008 | Cholette |
| 2010/0317956 | A1 | 12/2010 | Kartush |
| 2011/0034826 | A1* | 2/2011 | Notz et al. .......... 600/554 |

FOREIGN PATENT DOCUMENTS

| | | |
|---|---|---|
| EP | 2 637 736 | 4/2015 |
| WO | 00/16851 | 3/2000 |
| WO | 01/12089 A1 | 2/2001 |
| WO | 2006086367 A1 | 8/2006 |
| WO | 2009124726 A1 | 10/2009 |
| WO | 2010/035203 | 4/2010 |

OTHER PUBLICATIONS

Calancie, Bill and Nathan Lebwhol "Stimulus-Evoked EMG Monitoring During Transpedicular Lumbosacral Spine Instrumentation, Initial Clinical Results" Spine, vol. 19, No. 24, Apr. 6, 1994 (pp. 2780-2786).

Cheung, Albert T., Alberto Pochettino, Michael L. McGarvey, Jehangir J. Appoo, Ronald M. Fairman, Jeffrey P. Carpenter, William G. Moser, Edward Y. Woo, and Joseph E. Bavaria "Strategies to Manage Paraplegia Risk After Endovascular Stent Repair of Descending Thoracic Aortic Aneurysms" Science Direct—The Annuals of Thoracic Surgery, Apr. 21, 2005 (2 pages).

Deletis, Vedran and David B. Vodusek "Intraoperative Recording of the Bulbocavernosus Reflex [Clinical Studies]" (Ovid) Neurosurgery Online, vol. 40(1), http:/gateway.ut.ovid.com.ezproxy.hsclib.sunysb.edu/gwl/ovidweb.cgi, Jan. 1997 (pp. 88-93).

Dong, Charles C.J., David B. MacDonald, Ryojo Akagami, Brian Westerberg, Ahmed AlKhani, Imad Kanaan, and Maher Hassounah "Intraoperative Facial Motor Evoked Potential Monitoring with Transcranial Electrical Stimulation During Skull Base Surgery" Clinical Neurophysiology 116 2005, International Federation of Clinical Neurophysiology, Elsevier Ireland, Ltd. Sep. 13, 2004 (pp. 588-596).

Kartush, Jack M., Malcolm A. Graham, and Kenneth R. Bouchard "Intraoperative Facial Nerve Monitoring at Michigan Ear Institute" www.michiganear.com/library/F/facemon.pdf, Feb. 20, 1998 (10 pages).

Krassioukov, Andre, Roger Sarjeantm Homan Arkia, and Michael G. Fehlings "Multimodality Intraoperative Monitoring During Complex Lumbosacral Procedures: indications, techniques, and long-term follow-up review of 61 consecutive cases" J. Neurosurg: Spine, vol. 1, Oct. 2004 (pp. 243-253).

Kurstjens, G.A.M., A. Borau, A. Rodriguez, N.J.M. Rijkoff and T. Sinkjaer "Intraoperative Recording of Electroneurographic Signals From Cuff Electrodes on Extradural Sacral Roots in Spinal Cord Injured Patients" The Journal of Urology, vol. 174, Oct. 2005 (pp. 1482-1487).

Lopez, Jamie R., Steve D. Chang, and Gary K. Steinberg "The Use of Electrophysiological Monitoring in the Intraoperative Management of Intracranial Aneurysms" Jul. 13, 1998, J. Neurol. Neurosurg. Psychiatry vol. 66, 1999 (pp. 189-196).

Matz, Paul G., Charles Cobbs and Michael S. Berger "Intraoperative Cortical Mapping as a Guide to the Surgical Resection of Gliomas" Journal of Neuro-Oncology, vol. 42, 1999 (pp. 233-245).

Schmid, Daniel M., A. Curt, D. Hauri, and B. Schurch "Motor Evoked Potentials (MEP) and Evoked Pressure Curves (EPC) From the Urethral Compressive Musculature (UCM) by Functional Magnetic Stimulation in Healthy Volunteers and Patients with Neurogenic Incontinence" Neurology and Urodynamics, vol. 24, 2005 (pp. 117-124).

NIM-Response™—Nerve Integrity Monitor—Inoperative EMG Monitor—User's Guide—Medtronic XOMED, Copyright 2000, pp. 1-50.

Complaint, *Propep Surgical, L.L.C.* v. *Medtronic Xomed, Inc.*; Case No. D-1-GN-15-001413, filed in the District Court, Travis County, Tx (dated Apr. 10, 2015) (13 Pages).

Affidavit of Jon Schiff in Support of Plaintiff's Response to Defedant's Motion to Dismiss, Civil Action No. 1:15-cv-00356-SS, filed Jun. 11, 2015, pp. 1-42.

Declaration signed Dec. 15, 2015 and Dec. 16, 2015 by Randy Fagin; Jon Schif and Jann Bonfils-Rasmussen, filed in U.S. Appl. No. 13/107,855 and exhibits (50 pages).

Medtronic's Motion for Summary Judgment dated Jun. 23, 2016, 29 pages. The following are some of its exhibits.

Exhibit 1, Excerpts of Jan. 28, 2016 deposition of ProPep employee and co-founder, Jann Bonfils-Rasmussen, 41 pages.

Exhibit 2—Excerpts of Feb. 5, 2016 deposition of ProPep co-founder, Dr. Randy Fagin, pp. 32 pages.

Exhibit 3—Excerpts of Mar. 22, 2016 deposition of ProPep co-founder, Jon Schiff, 37 pages.

Exhibit 7—Excerpts of Mar. 30, 2016 deposition of third-party, Cadwell Industries, 15 pages.

Exhibit 8—2004 brochure from third-party, Intuitive Surgical, 7 pages.

Exhibit 10—Poster describing and showing ProPep's nerve monitoring system that ProPep testified was presented by Dr. Fagin in 2007, 2 pages.

Exhibit 11—Abstract published in the "Journal of Urology" (Sep. 2007), 3 pages.

Exhibit 14—ProPep presentation entitled "System and Method for Laparoscopic Nerve Detection During Radical Prostatectomy" ("Nerve Detection Presentation"). Deposition Exhibit 518, which is referenced in Rasmussen's (Jan. 28, 2016) testimony on p. 190, is another copy of the Nerve Detection Presentation, 18 pages.

Exhibit 16—Medtronic's Supplemental Interrogatory Answers, 14 pages. 2016.

(56) References Cited

OTHER PUBLICATIONS

Exhibit 18—Page from ProPep's website describing the video presentation at the 2010 World Robotic Urology Symposium, 3 pages.
Exhibit 19—Brochure from the 2010 World Robotic Urology Symposium, 17 pages.
Exhibit 21, Brochure from the 2011 International Robotic Urology Symposium, 15 pages.
Exhibit 22—A screen shot from the website on which ProPep's CEO posted video of the surgery using ProPep's nerve monitoring system that was broadcast live at the 2011 International Robotic Urology Symposium, 5 pages.
Exhibit 23, Brochure from and schedule for the 2011 International Robotic Prostatectomy Symposium, 21 pages.
Exhibit 24, Screen shot from a website on which a video describing all components of ProPep's nerve monitoring system,(Exbit 525 from Jan. 28, 2016 deposition of Rasmussen), 5 pages.
Exhibit 25—Screen shot showing that ProPep posted the same video as Exhibit 24 on YouTube on May 11, 2011, 3 pages.
Exhibit 26—ProPep's answer to Medtronic's second set of interrogatories, dated Jan. 25, 2016, 7 pages.
Exhibit 27—Photographs of ProPep's nerve monitoring system on display at the 2011 annual meeting of the American Urology Association ("AUA"), 11 pages.
Exhibit 28—Draft invitation to doctors to learn about ProPep's nerve monitoring system at the 2011 AUA meeting, 2 pages.
Exhibit 29—Excerpts from the Apr. 26, 2016 deposition of ProPep's CEO, Tom Stone, 16 pages.
Plaintiff Propep, LLC's Response to Defendant Medtronic Xomed, Inc.'s Motion for Summary Judgment, dated Jul. 21, 2016 (28 pages).
Defendant Medtronic Xomed Inc.'s Reply in Suppport of its Motion for Summary Judgment; dated Jul. 27, 2016 (11 pages).
Defendant Medtronic Xomed, Inc.'s Reply in Support of Its Motion for Summary Judgment, Jul. 27, 2016, 11 pages.
Plaintiff Propep, L.L.C.'s Response to Defendant Medtronic Xomed, Inc.'s Motion for Summary Judgment, Jul. 21, 2016, 28 pages.
PCT International Search Report for PCT/US2011/032888 dated Aug. 22, 2011 (17 pages).
Exhibit 6—Frequently Asked Questions page of ProPep's website, 5 pages. (Jun. 23, 2016).
Exhibit 20—ProPep press release and Austin Business Journal article relating to ProPep's receipt of the Tech Innovation award, 4 pages. (Jun. 23, 2016).
Complaint styled, *Propep Surgical, L.L.C.*, Plaintiff v. *Medtronic Xomed, Inc.*, Defendant in the 200th Judical District Court, Travis County, Texas (13 pages) (Apr. 10, 2015).

\* cited by examiner

INTERFACE MODULE FOR USE WITH NERVE MONITORING AND ELECTROSURGERY

BACKGROUND

Electrophysiological monitoring assists a surgeon in locating nerves within an obscured surgical field, as well as preserving and assessing nerve function in real-time during surgery. To this end, nerve integrity monitoring is commonly employed to monitor electromyographic (EMG) activity. During nerve integrity monitoring, sensing or recording electrodes are coupled to appropriate tissue (e.g., cranial muscles innervated or controlled by the nerve of interest, peripheral nerve, spinal cord, brainstem, etc.) to sense EMG activity. Stimulation, for example electrical stimulation or mechanical stimulation, can cause excitement of the tissue. During electrical stimulation, a stimulation probe applies a stimulation signal near the area where the subject nerve may be located. If the stimulation probe contacts or is reasonably near the nerve, the applied stimulation signal is transmitted through the nerve to excite the innervated tissue. In mechanical stimulation, direct physical contact of the appropriate tissue can cause excitement of the tissue. In any event, excitement of the related tissue generates an electrical impulse that is sensed by the recording electrodes (or other sensing device). The recording electrode(s) signal the sensed electrical impulse information to the surgeon for interpretation in the context of determining EMG activity. For example, the EMG activity can be displayed on a monitor and/or presented audibly.

Nerve integrity monitoring is useful for a multitude of different surgical procedures or evaluations that involve or relate to nerve tissue, muscle tissue, or recording of neurogenic potential. For example, various head and neck surgical procedures (e.g. parotidectomy and thyroidectomy) require locating and identifying cranial and peripheral motor nerves. In some instances, an electrosurgical unit is used to perform these surgical procedures. Current electrosurgical units include a conductive tip or needle that serves as one electrode in an electrical circuit which is completed via a grounding electrode coupled to the patient. Incision of tissue is accomplished by applying a source of electrical energy (most commonly, a radio-frequency generator) to the tip. Upon application of the tip to the tissue, a voltage gradient is created, thereby inducing current flow and related heat generation at the point of contact. With sufficiently high levels of electrical energy, the heat generated is sufficient to cut the tissue and, advantageously, to simultaneously cauterize severed blood vessels.

Due to the levels of electrical energy generated by electrosurgical units, systems for nerve integrity monitoring experience a large amount of electrical interference when used during electrosurgical procedures. The electrical interference can create incorrect neurogenic (nerve tissue) or myogenic (muscle tissue) signals. For example, during EMG monitoring, electrosurgical activity can create artifacts (e.g., false positives) as well as introduce a significant amount of noise in the nerve integrity monitoring system. As a result, current techniques involve using a probe to mute all channels of the nerve integrity monitoring system during an electrosurgical procedure. Thus, monitoring of EMG activity is typically suspended during operation of the electrosurgical unit. In order for a surgeon to prevent cutting a nerve with the electrosurgical unit, the surgeon will cut for a brief period and then stop cutting such that nerve integrity monitoring can be restored. If no EMG activity is detected, the surgeon can then cut for another brief period, while pausing intermittently to restore nerve integrity monitoring so as to prevent from cutting a nerve. This process is repeated until the surgeon is completed with the electrosurgical procedure. Without being able to monitor EMG activity during an electrosurgical procedure, the electrosurgical procedure can be cumbersome and time consuming.

SUMMARY

Concepts presented herein relate to an interface module that can be electrically coupled to an electrical stimulation generator, a radio frequency generator and an instrument. A selection module is coupled to the interface module and operates in a first mode to deliver electrical stimulation signals from the electrical stimulation generator to the instrument and in a second mode to deliver and/or disable radio frequency signals from the radio frequency generator to the instrument.

DETAILED DESCRIPTION

Figure 1:
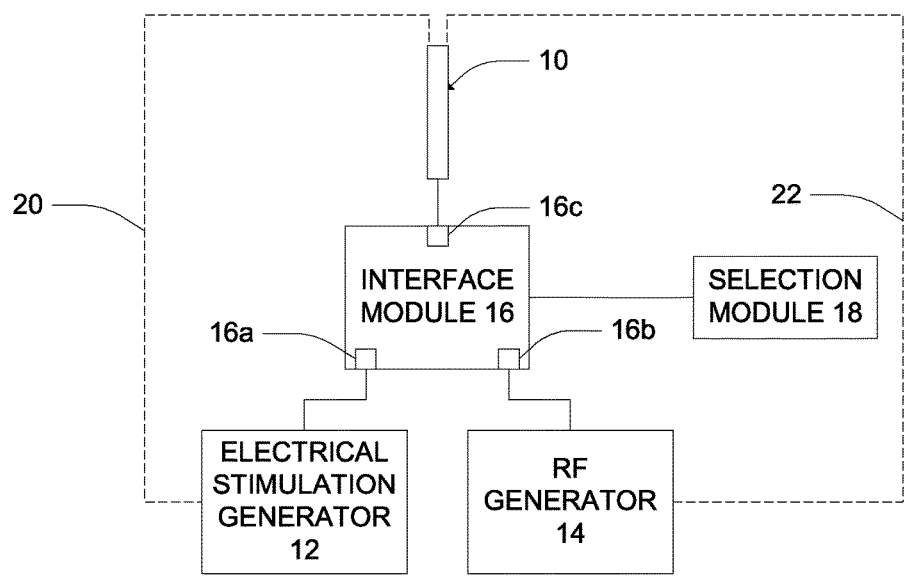
FIG. 1 is a schematic block diagram of an interface module selectively delivering electrical stimulation signals and radio frequency signals to an instrument.

FIG. 1 is a schematic block diagram of an instrument 10 for selectively applying signals received from an electrical stimulation generator 12 and a radio frequency (RF) generator 14 to tissue of interest in a surgical procedure. An interface module 16 is electrically coupled to the stimulation generator 12 and the RF generator 14 to selectively operate in a plurality of modes to deliver a desired output to the instrument 10. In particular, interface module 16 includes a first input 16a electrically coupled to the electrical stimulation generator 12, a second input 16b electrically coupled to RF generator 14 and an output 16c electrically coupled to instrument 10.

A selection module (e.g., a switch or network) 18 is coupled to interface module 16 and operates to selectively deliver one of electrical stimulation signals and RF signals provided by electrical stimulation generator 12 and RF generator 14, respectively, to instrument 10. In particular, selection module 18 is configured to complete either a first, electrical stimulation circuit 20 or a second, RF circuit 22. As such, when instrument 10 is brought into contact with tissue of a patient and electrical stimulation circuit 20 is complete, electrical stimulation signals from electrical stimulation generator 12 are delivered to the tissue. Alternatively, when RF circuit 22 is complete, radio frequency signals from RF generator 14 are delivered to the tissue. Interface module 16 can further be coupled to recording electrodes that can provide signals that are indicative of contact between instrument 10 and a nerve or muscle.

Instrument 10 can be any instrument that electrically interfaces with a patient to perform nerve monitoring and/or electrosurgery. In one embodiment, instrument 10 can be a bipolar forceps, a laparoscopic bipolar instrument or a monopolar cautery pencil. In any event, instrument 10 can include an integrated nerve stimulating probe as well as a working tip appropriate for a desired application such as surgery.

In one embodiment, electrical stimulation generator 12 is part of a NIM-Response® 3.0 nerve monitoring system available from Medtronic Xomed, Inc. of Jacksonville, Fla., and configured to deliver electrical stimulation signals to instrument 10 so as to excite tissue in contact with instrument 10. In one embodiment, the electrical stimulation signals provided by electrical stimulation generator 12 are of sufficient strength so as to stimulate associated tissue yet inherently safe so as to prevent physical trauma to the associated tissue.

In one embodiment, RF generator 14 can be part of an electrosurgical unit (ESU) configured to manipulate tissue, for example through cutting, cauterizing and hemostasis. Example ESUs are available through Valleylab of Boulder, Colo.; ERBE of Marietta, Ga.; ConMed Corporation of Utica, N.Y.; Gyrus ACMI of Southborough; Mass. and Megadyne of Draper, Utah. RF generator 14 can be configured to achieve various different tissue effects, as desired. In one embodiment, RF generator is configured to operate to delivery signals at a rate between 500-3,300 KHz at various voltage levels.

Interface module 16 integrates electrical stimulation generator 12 and RF generator 14. To this end, interface module 16 can be equipped to receive cabling from electrical stimulation generator 12, RF generator 14 and instrument 10. Interface module 16 can further be equipped to receive input from and/or provide output to other devices as desired.

Selection module 18 can take many forms including a manual switch, electrical switch or electrical network, to selectively direct and deliver signals from electrical stimulation generator 12 and RF generator 14. In one embodiment, selection module 18 can be a mechanical switch directly integrated into instrument 10 so that a user can easily select what signals are sent to instrument 10 while operating instrument 10. For example, instrument 10 may include a handle with selection module 18 maintained within the handle. In this embodiment, two way communication is provided between instrument 10 and interface module 16 so that selection module 18 notifies interface module 16 of a desired signal to be sent to instrument 10. In a further embodiment, selection module 18 can be directly coupled to interface module 16. Example mechanical switches include dome switches, rocker switches, toggle switches, etc. In a still further embodiment, selection module 18 can be an electrical switch. The electrical switch can be configured to interleave signals to instrument 10 so as to give the appearance to a user that both signals from electrical stimulation generator 12 and RF generator 14 are simultaneous, for example by periodically switching signals delivered to instrument 10 on a short time scale (e.g. milliseconds) into an alternating pattern. In another embodiment, the interface module 16 continuously combines and directs electrical stimulation signals and radio frequency signals in the output signals. In still a further embodiment, selection module 18 can be formed of a combination of mechanical and electrical switches. For example, an electrical switch can continuously interleave electrical stimulation signals into output signals that are sent to instrument 10 while a mechanical switch determines whether signals from RF generator 14 are sent to instrument 10. In yet a further embodiment, selection module 18 can be an electrical network configured to select a signal that is delivered to instrument 10, for example as a function of a frequency of the signal or alternatively combine electrical stimulation signals and RF signals into an output signal.

In a further embodiment, interface module 16 can be capable of two, three or more modes of operation. For example, RF generator 14 can provide multiple distinct operational signals when used as an electrosurgical unit. In one particular embodiment, these RF generator signals are configured for both cutting and coagulation. In this instance, interface module 16 can be configured to operate in three separate modes, namely an electrical stimulation mode, (thus delivering stimulation signals from electrical stimulation generator 12) an RF cutting mode (thus delivering cutting signals from RF generator 14) and an RF coagulation mode (thus delivering coagulation signals from RF generator 14).

In still further embodiments, interface module 16 can include a default mode of operation. For example, interface module 16 can be configured to deliver signals from electrical stimulation generator 12 when a user has not actively selected a desired mode of operation. As discussed above, signals from electrical stimulation generator 12 operates in an inherently safe mode that does not provide physical trauma to tissue in contact with instrument 10. By utilizing a default mode for delivering electrical stimulation, accidental delivery of RF signals to instrument 10 can be prevented. In an alternative default mode, interface module 16 prevents any signals from being transmitted to instrument 10. In yet a further embodiment, interface module 16 can prevent signals sent from electrical stimulation generation 12 upon an indication that instrument 10 is proximate and/or contacts a nerve.

In any event, selection module 18 operates to selectively complete electrical stimulation circuit 20 or RF circuit 22. To this end, circuits 20 and 22 can be configured for different modalities, such as monopolar, bipolar and/or combinations thereof. For example, in a monopolar modality, circuit 20 can include one or more recording electrodes coupled to tissue of a patient. When circuit 20 is complete, current passes from electrical stimulation generator 12, through interface module 16 and to instrument 10, in contact with tissue. Current then passes through tissue from the point of contact with instrument 10 to the point of coupling to the one or more recording electrodes. Current then passes from the recording electrodes back to electrical stimulation generator 12. In an alternative embodiment, instrument 10 may be a bipolar instrument that includes two electrodes, one serving as an active electrode and one serving as a return electrode. In this case, current flows from electrical stimulation generator 12, through the interface module 16 and to the active electrode of instrument 10. Current then passes through the tissue from the point of contact with the active electrode to the point of contact with the return electrode and back through the return electrode, instrument 10, interface module 16 and to electrical stimulation generator 12. Similarly, RF circuit 22 can include a dispersive pad coupled to tissue in a monopolar configuration and/or instrument 10 can include multiple electrodes in a bipolar configuration so as to complete circuit 22 through tissue of the patient.

Figure 2:
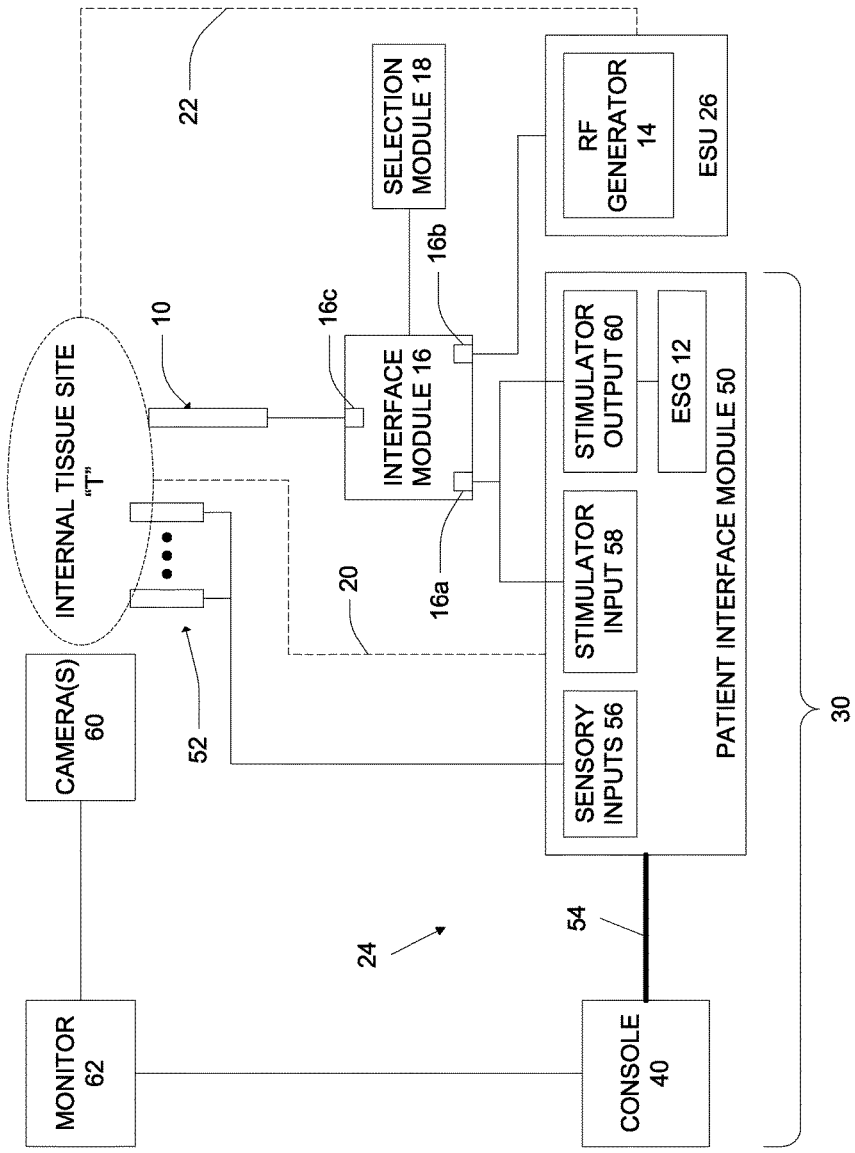
FIG. 2 is a schematic block diagram of a surgical system including an interface module coupled to a nerve integrity monitoring system and an electrosurgical unit.

FIG. 2 is a schematic block diagram of a surgical environment utilizing specific implementations of components illustrated in FIG. 1 to selectively perform nerve monitoring and electrosurgery at an internal target tissue site "T". In one embodiment, the internal target tissue site "T" is accessed laparoscopically and surgery is performed using a surgical robot such as the DaVinci robot available from Intuitive Surgical of Sunnyvale, Calif. In this case, instrument 10 is a wristed instrument coupled to the surgical robot and capable of control by the robot. Electrical stimulation generator 12 is embodied within a nerve monitoring system 24 and RF generator 14 is embodied within an electrosurgical unit (ESU) 26. Interface module 16 is coupled to both nerve monitoring system 24 and electrosurgical unit 26 through inputs 16a and 16b as discussed above. Interface module 16 is also coupled to instrument 10 through output 16c. Selection module 18 is operatively coupled to interface module 16 to indicate desired signals to be delivered to instrument 10, so as to selectively complete circuits 20 and 22 (schematically shown).

In general terms, the nerve monitoring system 24 is configured to assist in and perform nerve integrity monitoring for virtually any nerve/muscle combination of the human anatomy, as well as recording nerve potential. The system 24 includes a control unit 30, which can assume a wide variety of forms and in one embodiment includes a console 40 and a patient interface module 50. The ESU 26 generates current that is sent to surgical instrument 10 for cutting or otherwise manipulating tissue of a patient.

System 24 includes one or more sensing probes 52, which can be any type of sensing device such as an electrode and can operate to complete circuit 20 in a monopolar configuration. In a laporoscopic surgical environment, sensing probes 52 can be coupled to tissue internal to a patient through a suitable introducer such as a cannula, trocar, etc. The control unit 30 facilitates stimulation of the instrument 10, as well as processes all information generated by instrument 10, sensing probes 52 and other components (not shown) during use. The instrument 10 and the control unit 30 are adapted to allow control and variation of a stimulus energy delivered to, and thus a stimulus level delivered by, the instrument 10. Further, the control unit 30 processes information (e.g., patient response) received from instrument 10 and/or sensing probes 52 resulting from delivered stimulation.

Using the sensing probes 52, the system 24 performs monitoring based upon recorded EMG activity in response to an electrical current energy delivered by the instrument 10 and/or physical manipulation of tissue. With the one embodiment of FIG. 2, the console 40 and the patient interface module 50 are provided as separate components, communicatively coupled by a cable 54. Alternatively, a wireless link can be employed. Further, the console 40 and the patient interface module 50 can be provided as a single device. In basic terms, however, the patient interface module 50 serves to promote easy connection of stimulus/sensory components (such as the instrument 10 and sensing probes 52), as well as to manage incoming and outgoing electrical signals. The console 40, in turn, interprets incoming signals (e.g., impulses sensed by sensing probes 52), displays information desired by a user, provides audible feedback of signals, presents a user interface (such as by including, for example, a touch screen), and delivers a stimulation energy to the instrument 10 pursuant to control signals from the instrument 10 (via connection to the patient interface module 50), as well as other tasks as desired.

As previously described, the patient interface module 50 communicates with the console 40 through the cable 54 information to and from the instrument 10, as well as information from the sensing probes 52. In effect, the patient interface module 50 serves to connect the patient (e.g., at tissue site "T") to the console 40. To this end, and in one embodiment, the patient interface module 50 includes one or more (preferably eight) sensory inputs 56, such as pairs of electrode inputs electrically coupled to receive signals from the sensing probes 52 (referenced generally in FIG. 2). In addition, the patient interface module 50 provides a stimulator input port 58 (referenced generally in FIG. 2) and a stimulator output port 60 (referenced generally in FIG. 2). The stimulator input port 58 receives control signals from the instrument 10 relating to desired stimulation levels and/or other activities, whereas the stimulator output port 60 facilitates delivery of stimulation energy from the electrical stimulation generator 12 to the instrument 10. The patient interface module 50 can further provide additional component port(s), such as a ground (or return electrode) jack, auxiliary ports for additional stimulator probe assemblies, etc.

The sensing probes 52 are coupled to the patient (e.g., selected tissue) to provide signals to the patient interface module 50. In one embodiment, the plurality of probes 52 includes eight probes that are electronically coupled to sensory inputs 56. In normal operation, the probes 52 sense electrical signals from the patient and send the signals to patient interface module 50. These signals include an electrical impulse from patient tissue, which is indicative of EMG activity (e.g., a bio-electric response) in the patient. Upon sensing that instrument 10 is proximate and/or contacting a nerve so as to create EMG activity (e.g., as a result of signals from ESG 12 and/or ESU 26), sensing probes 52 can provide an indication to interface module 16 that will disable any further signals from ESU 26 being transmitted to tissue site "T" through instrument 10. As a result, damage to nerves in tissue site "T" can be prevented by automatically disabling operation of ESU 26 (e.g., by suppressing its signals). In a further embodiment, interface module 16 can further provide an alert (e.g., an audible and/or visual signal) that sensing probes 52 are sensing EMG activity.

ESU 26 can be configured to perform various electrosurgical modalities such as monopolar, bipolar and/or combinations thereof. Moreover, ESU 26 can be configured to deliver different types of RF signals so as to achieve a desired tissue effect. To this end, various waveforms and/or power settings can be applied to instrument 10 through interface module 16 as desired. Additionally, instrument 10 can be equipped with a tip desired for a particular application of signals from ESU 26.

In a further embodiment, one or more cameras 60 are positioned so as to provide visual information of the surgical site to assist the surgeon in performing the desired surgical procedure. The one or more cameras 60 can also be introduced to site "T" laparoscopically. Video data from the one or more cameras 60 can be provided to a monitor 62, along with video data from console 40. To this end, the surgeon is provided with both visual information of the surgical site as well as visual information indicative of recorded responses from sensing probes 52 and/or instrument 10. By selectively providing stimulation signals and RF signals, the surgeon, through use of monitor 62, can visually check whether a targeted site is a nerve or whether RF signals can be sent so as to cut the targeted tissue. As such, a surgeon can quickly discern and cut targeted tissue.

Although the present disclosure has been described with reference to preferred embodiments, workers skilled in the art will recognize that changes can be made in form and detail without departing from the spirit and scope of the present disclosure.

What is claimed is:

1. A surgical system for use on tissue at a target site, comprising:
    an instrument;
    an electrical stimulation generator configured to generate electrical stimulation signals;
    an electrosurgical unit configured to generate radio frequency signals;
    an interface module electrically coupled to the instrument, the electrical stimulation generator and the electrosurgical unit, the interface module configured to receive an indication of a bio-electric response caused by stimulation of the tissue from the electrical stimulation signals;

a first circuit including the instrument, the electrical stimulation generator and the interface module;

a second circuit including the instrument, the electrosurgical unit and the interface module; and a selection module electrically coupled to the interface module and utilizing an electronic switch configured to selectively complete one of the first circuit and the second circuit so as to automatically interleave the electrical stimulation signals and the radio frequency signals delivered by the instrument into an alternating pattern, wherein upon receiving the indication, the interface module automatically disables the second circuit to prevent radio frequency signals from being sent to the instrument.

2. The surgical system of claim 1 wherein the instrument is one of a bipolar forceps, a laparoscopic bipolar instrument, a monopolar cautery pencil and a wristed instrument.

3. The surgical system of claim 1 wherein the selection module is coupled to the instrument.

4. The surgical system of claim 1 wherein the selection module is electrically coupled to the interface module and configured to disconnect the second circuit.

5. The surgical system of claim 1 wherein the selection module is electrically coupled to the interface module to provide a signal indicative of electrical activity at the target site.

6. The surgical system of claim 1, further comprising one or more recording electrodes coupled to the tissue and configured to record the bio-electric response from the tissue, the bio-electric response generated from electrical stimulation signals delivered to the tissue and wherein the one or more recording electrodes form part of the first circuit.

7. The surgical system of claim 1, further comprising one or more recording electrodes coupled to the tissue and configured to record the bio-electric response from the tissue.

8. The surgical system of claim 1, further comprising one or more recording electrodes coupled to tissue and configured to record the bio-electric response generated from the electrical stimulation signals delivered to the tissue.

9. The system of claim 1, wherein the electrosurgical unit is configured to deliver both cutting signals and coagulation of signals to the instrument.

10. The system of claim 1, wherein the signals are interleaved in the order of milliseconds.

11. A surgical system for use on tissue at a target site, comprising:

an instrument;

an electrical stimulation generator configured to generate electrical stimulation signals;

an electrosurgical unit configured to generate radio frequency signals;

an interface module electrically coupled to the instrument, the electrical stimulation generator and the electrosurgical unit, the interface module configured to receive an indication of a bio-electric response caused by stimulation of the tissue from the electrical stimulation signals;

a first circuit including the instrument, the electrical stimulation generator and the interface module;

a second circuit including the instrument, the electrosurgical unit and the interface module; and a selection module electrically coupled to the interface module and utilizing an electronic switch configured to selectively complete one of the first circuit and the second circuit so as to automatically interleave the electrical stimulation signals and the radio frequency signals delivered by the instrument into an alternating pattern on the order of milliseconds, wherein upon receiving the indication, the interface module automatically disables the second circuit to prevent radio frequency signals from being sent to the instrument.

12. The surgical system of claim 11, wherein the instrument is one of a bipolar forceps, a laparoscopic bipolar instrument, a monopolar cautery pencil and a wristed instrument.

13. The surgical system of claim 11, wherein the selection module is coupled to the instrument.

14. The surgical system of claim 11, wherein the selection module is electrically coupled to the interface module and configured to disconnect the second circuit.

15. The surgical system of claim 11, wherein the selection module is electrically coupled to the interface module to provide a signal indicative of electrical activity at the target site.

16. The surgical system of claim 11, further comprising one or more recording electrodes coupled to the tissue and configured to record the bio-electric response from the tissue, the bio-electric response generated from electrical stimulation signals delivered to the tissue and wherein the one or more recording electrodes form part of the first circuit.

17. The surgical system of claim 11, further comprising one or more recording electrodes coupled to the tissue and configured to record the bio-electric response from the tissue.

18. The surgical system of claim 11, further comprising one or more recording electrodes coupled to tissue and configured to record the bio-electric response generated from the electrical stimulation signals delivered to the tissue.

19. The system of claim 11, wherein the electrosurgical unit is configured to deliver both cutting signals and coagulation of signals to the instrument.

* * * * *